United States Patent [19]

Dillon et al.

[11] Patent Number: 5,206,171
[45] Date of Patent: Apr. 27, 1993

[54] PROGRAMMABLE AUTOMATED INOCULATOR/REPLICATOR

[75] Inventors: Jo-Anne Dillon; Kwok-Him Yeung, both of Ottawa; Sam S. Lightstone, Kingston, all of Canada

[73] Assignee: Her Majesty the Queen in right of Canada, Ottawa, Canada

[21] Appl. No.: 628,156

[22] Filed: Dec. 17, 1990

[51] Int. Cl.$^5$ ............................................. C12M 1/32
[52] U.S. Cl. ...................... 435/293; 435/298; 435/300; 435/809; 422/63; 422/65
[58] Field of Search ............... 435/30, 287, 291, 292, 435/293, 297, 298, 299–301, 310, 809; 422/63–65, 99, 100; 73/863.01, 864.23; 414/749, 750, 751, 222; 198/468.01, 468.9; 53/50, 468, 471, 485, 109, 167, 250, 281, 282, 309, 381.4

[56] References Cited

U.S. PATENT DOCUMENTS

| | | | |
|---|---|---|---|
| 3,704,568 | 12/1972 | Duhring et al. | 53/109 |
| 3,708,264 | 1/1973 | Jottier | 422/65 |
| 4,142,286 | 3/1979 | Covington et al. | 422/63 |
| 4,166,094 | 8/1979 | Froehlich et al. | 422/64 |
| 4,170,861 | 10/1979 | Snyder et al. | 53/109 |
| 4,259,289 | 3/1981 | Curry et al. | 422/64 |
| 4,269,803 | 5/1981 | Jessop | 422/63 |
| 4,299,796 | 11/1981 | Hogen Esch | 422/65 |
| 4,301,116 | 11/1981 | Ida et al. | 422/65 |
| 4,322,216 | 3/1982 | Lillig et al. | 422/64 |
| 4,413,534 | 11/1983 | Tomoff et al. | 422/65 |
| 4,480,031 | 10/1984 | Shaw | 435/292 |
| 4,554,839 | 11/1985 | Hewett et al. | 422/65 |

FOREIGN PATENT DOCUMENTS

| | | | |
|---|---|---|---|
| 0252471 | 1/1988 | European Pat. Off. | |
| 1115480 | 6/1986 | Japan | 436/287 |
| 2267642 | 11/1987 | Japan | 435/287 |
| 2269757 | 11/1987 | Japan | 435/287 |
| 3102663 | 5/1988 | Japan | 435/287 |
| 2018288 | 10/1979 | United Kingdom | 435/287 |
| 8807710 | 10/1988 | World Int. Prop. O. | |

OTHER PUBLICATIONS

Zymark, "PxTechnology, Zymate Laboratory Automation Systems" Noc. 17, 1986 pp. 1'43.

*Primary Examiner*—Michael G. Wityshyn
*Assistant Examiner*—William H. Beisner
*Attorney, Agent, or Firm*—Jones, Tullar & Cooper

[57] ABSTRACT

Laboratory apparatus for performing repetitive tacks includes a table and first and second bearing ways below the table. First and second carriages are mounted on corresponding bearing ways for independent motion therealong, the second carrriage moving in a plane below and parallel to the first carriage. An independently operable transfer device moves objects between the table and a selected carriage or between the carriages, as desired, and apparatus is provided adjacent to the table for performing operations on objects located on the table or on the carriages, the transfer device, and the operating apparatus being capable of repetitive operation.

18 Claims, 7 Drawing Sheets

PROGRAMMABLE AUTOMATED INOCULATOR/REPLICATOR

This invention relates to a device for automatically and programmably performing a number of repetitive functions in a clinical microbiology laboratory. In particular it relates to a programmable automated inoculator and replicator device for use in such laboratories.

BACKGROUND OF THE INVENTION

A number of procedures performed in clinical microbiology laboratories involve repetitive, sequential, labour-intensive tasks utilizing trained technical personnel. For example, the personnel may be required to transfer samples between different pieces of equipment; they may have to simultaneously inoculate multiple bacterial cultures onto a sequential series of media; they may have to serially dilute various reagents; they may have to stain and destain bacterial specimens with several dyes; or they may have to dispense microbiological media into petri dishes. Although some of these procedures, such as media dispensation and serial dilution, have been automated, others including antimicrobial susceptibility testing by agar dilution have not. Examples of single-task automated systems usable in a clinical microbiology laboratory are found in U.S. Pat. Nos. 4,142,863; 4,166,094; 4,259,289; 4,269,803; 4,301,116; and 4,322,216.

SUMMARY OF THE INVENTION

The present invention has been designed so as to have a plurality of individually controllable functions available so that several dissimilar but routine microbiological procedures could be performed using the same piece of equipment. Simplicity of operation was essential for non-involved programming to perform such diverse tasks according to on-going requirements. The equipment according to the present invention utilizes a plurality of components providing multiple degrees of freedom, some or all of such components being used depending on the function to be performed.

One of the important functions that can be done on a repetitive basis is the precise, sequential delivery of multiple bacterial inocula, using any of a number of commercially available multiple inoculators, to a large number of individual media. Typically the inoculation process involves obtaining a fresh media plate (e.g. a petri dish), removing the plate cover, inoculating the media with bacterial cultures without contamination, replacing the cover, and stacking the plates. This set of steps may be repeated 60 to 100 times for each test procedure.

The apparatus of the present invention is inexpensive to produce and simple to operate, being particularly adaptable to computer control. It includes a removable table portion above a pair of fixed, parallel, elongated bearing ways, each of which supports a carriage for movement therealong. The carriages are movable independently of each other but they can, and will, move relative to each other in a particular sequence depending on the repetitive function being performed.

For the aforementioned inoculation procedure the table is adapted to receive a stack of sterile culture media plates (petri dishes) and it is also adapted to receive and stack the media plates following the inoculation thereof. The uppermost of the two carriages is adapted to receive and pass therethrough a media plate lowered from a source stack on the table and to retain the cover loosely resting thereon. The lowermost carriage is adapted to receive the media plate itself after it has passed through the uppermost carriage.

The apparatus also includes a vertically movable arm to which a multiple inoculator head can be secured. The lowermost carriage can move on its bearing ways to a work station at which the media plate is inoculated when the arm lowers the inoculator head into contact with the culture in the media plate. The arm is raised and the lowermost carriage moves back to below the uppermost carriage which, in the meantime, has moved to position the cover below the area of the table adapted to receive the inoculated plates. The inoculated plate on the lowermost carriage is raised into contact with the cover on the uppermost carriage and the covered plate is then raised into a receiving stack on the table. The apparatus is then ready to repeat the same function again. Clearly most of the boring, repetitive manual labour has been removed from this dreary procedure. All that an operator of the equipment has to do is to ensure that the apparatus has an adequate supply of media plates and inoculant, and to remove the inoculated plates once the stack thereof has reached its maximum height.

In addition to the vertical lift for the media plates and the laterally movable carriages the present invention also provides for a vertical lift device for the inoculant. It also provides for rotational means which can be used to rotationally move items on, or in close relation to, one or both carriages.

The invention can use up to five separate stepper drive means to achieve the desired movements, the motors being individually controlled. Electronic or optical sensors can be positioned at different critical locations within the system to help control operation of the system. The entire system can be controlled by a suitably programmed microcomputer and the computer can also be used to record system performance so that any operating problems could be diagnosed electronically.

With the addition of other appropriate sensors and supplementary computer software the system could be adapted to record bacterial growth on plates, analyze results and generate reports.

In summary, therefore the present invention may be broadly considered to provide laboratory apparatus for performing repetitive tasks comprising: frame means; first parallel bearing ways in the frame means; second parallel bearing ways in the frame means parallel to the first bearing ways; first carriage means supported by the first bearing ways for independent movement therealong; second carriage means supported by the second bearing ways for independent movement therealong; independently operable action means at a work station adjacent to or on one of the carriage means for manipulating an object carried thereby relative to the other carriage means; and means for coordinating the movement of the first and second carriage means, and the action means in accordance with the repetitive operations to be performed.

DESCRIPTION OF THE PREFERRED EMBODIMENT

Figure 1:
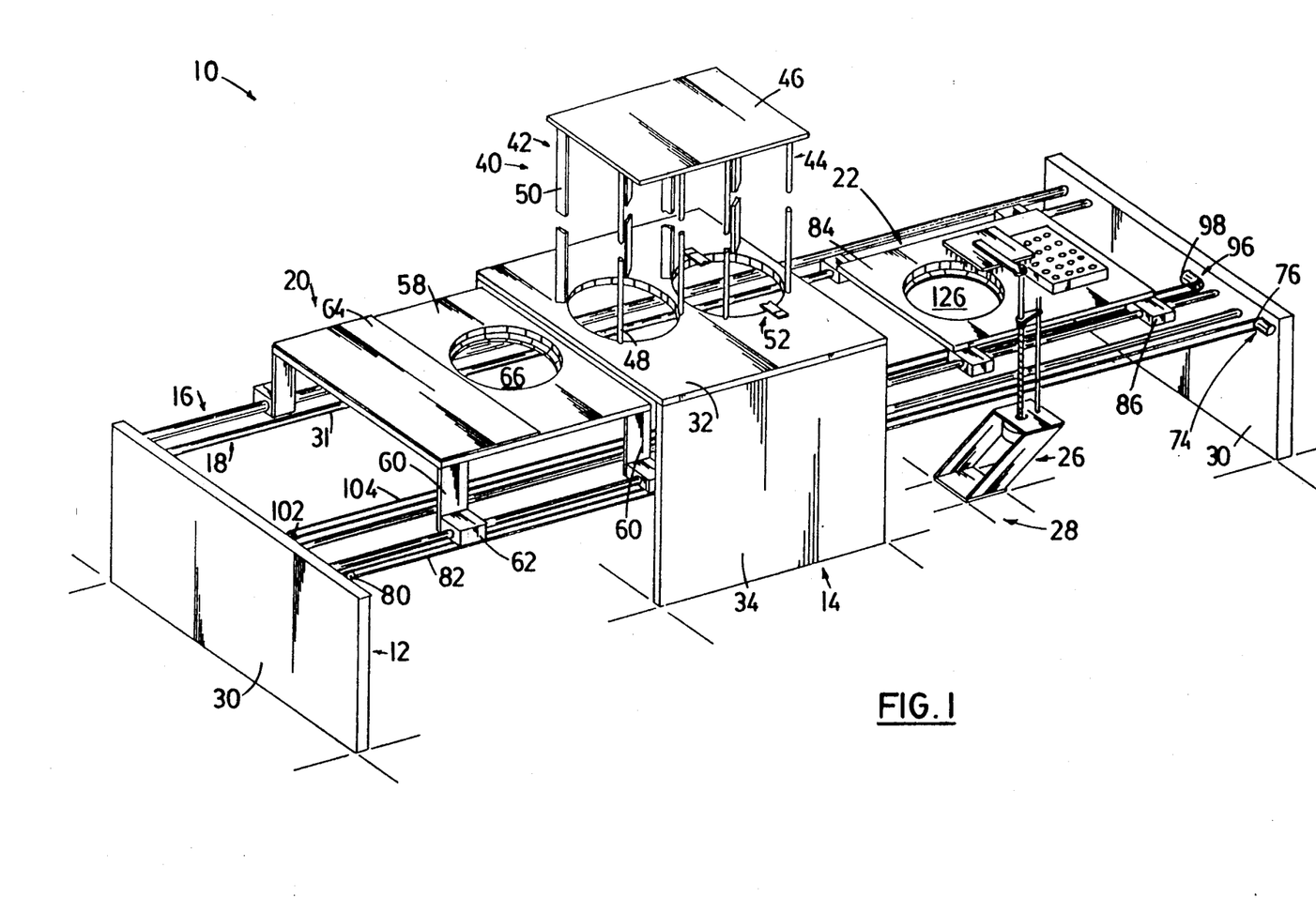
FIG. 1 is a perspective view of the apparatus of the present invention.

FIG. 1 illustrates in perspective the apparatus as developed for inoculating bacterial cultures onto a plurality of media plates, such as sterilized, covered petri dishes. The procedure is accomplished in a programmed, automated fashion, without physical input from an operator except for ensuring that there is a sufficient supply of media plates and inoculant and for removing the inoculated plates once a stack of them has accumulated at an output station of the apparatus. Variations of the apparatus will be described later.

The apparatus 10 may be seen to include a frame means 12 in which a table means 14 is removably located, a set of first parallel bearing ways 16 and a set of second parallel bearing ways 18 located inside and preferably in the same plane as the first bearing ways 16. A first carriage means 20 is supported by the first bearing ways 16 for independent movement therealong and below the table means 14 and a second carriage means 22 is supported by the second bearing ways 18 for independent movement therealong and below the first carriage means 20. Independently operable transfer means 24 is provided for transferring objects, such as media plates, between the carriage means 20,22 and the table means 14. Furthermore, an independently operable action means 26 is provided at a selected work station 28 for performing an operation on an object, such as a media plate. In this instance the action means 26 will be inoculating bacterial culture contained within each media plate. The structure of each component and the function thereof will now be described in greater detail, with specific reference to FIGS. 2 to 8.

Figure 2:
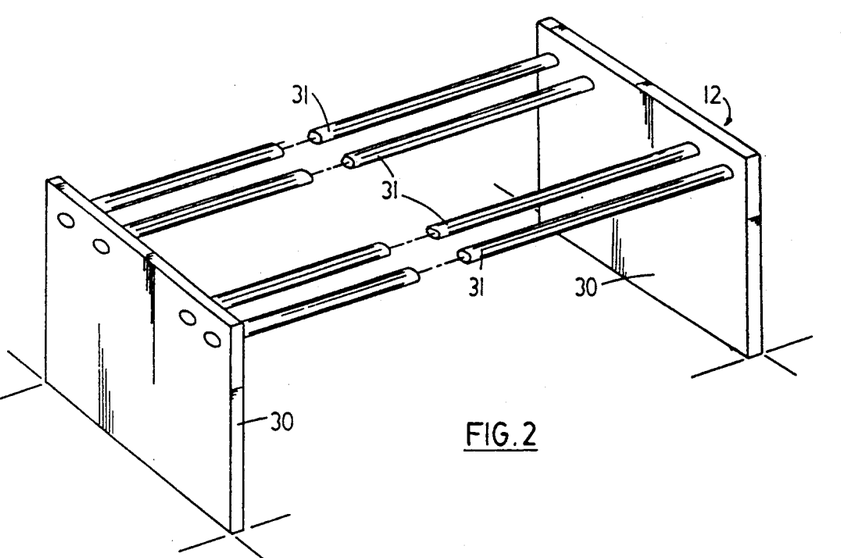
FIG. 2 is a partial perspective view of the frame means of the apparatus.

FIG. 2 shows the frame means 12 which includes vertically oriented end plates 30 which, in turn support the apparatus 10 on an appropriate work surface, such as a laboratory table. The end plates 30 support the bearing ways 16,18 therebetween in any conventional manner. Each bearing way is a cylindrical rod 31 adapted to cooperate with linear bearings carried by the carriage means, the bearing ways 16,18 being parallel to each other and preferably but not essentially being in the same plane.

Figure 3:
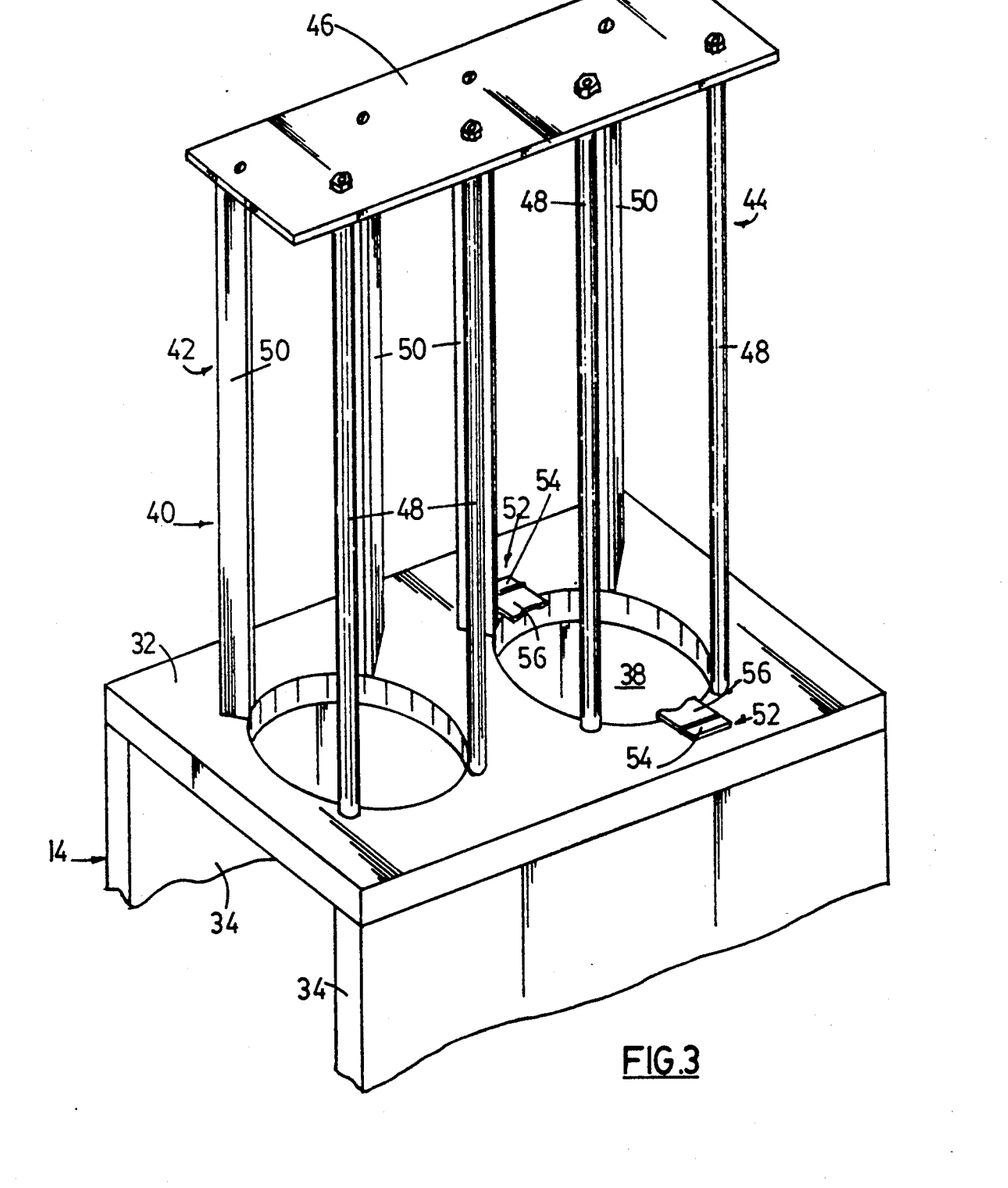
FIG. 3 is a partial perspective view of the table means of the apparatus.

FIG. 3 shows the table means 14 as including an upper plate 32 which is parallel to the bearing ways 16,18 and a pair of longitudinally extending side legs 34,34 which support the plate 32 above the work surface and the bearing ways 16,18. The legs 34,34 may just rest on the work surface or they may be secured or otherwise tied into the frame means 12. The table means 14 can be positioned anywhere longitudinally of the frame means 12 or; if desired depending on the operation to be performed, it can be removed completely and not used at all.

The plate 32 has two circular holes 36,38 extending vertically therethrough essentially on the centerline of the apparatus 10. Each hole 36,38 is of a diameter such that a circular covered media plate can pass therethrough without interference. If objects having other than a circular configuration are to be used then one could use a table means, not shown, having appropriately configured holes therethrough and which would be interchangeable with the table means 14. Alternatively, one could start with holes appropriately sized to the largest article to pass therethrough and use templates or inserts fittable within the holes to downsize or alter them to the desired configuration.

Rising above the upper plate 32, and secured thereto in a conventional manner is a guide structure 40 including adjacent guide cages 42,44 connected together by top plate 46. Each cage includes a pair of parallel vertical rods 48,48 and a pair of strengthening rectangular struts 50,50. The rods 48,48 and struts 50,50 are arranged about the corresponding hole 36,38 so as to be adjacent the edge thereof and so as to loosely contact the edge of circular media plates stacked on each other within the cages 42,44. The spacing between the adjacent upright members 48,48, 50,50 of each cage is such that a media plate can be rotated to pass therethrough for introduction to or removal from the apparatus of this invention In the embodiment as illustrated the cage 42 is intended to receive and hold a stack of non-inoculated media plates or petri dishes prior to being fed through the apparatus. The cage 44 is intended to receive and hold media plates that have been inoculated. Non-inoculated media plates will pass downwardly through hole 36 in a manner to be described and inoculated plates will be transferred upwardly through hole 38, also in a manner to be described. In order to prevent inoculated media plates from falling back downwardly the plate 32 is provided with a pair of pivotable support members 52, one portion 54 of which is secured to the plate 32 and the other portion 56 of which is hingedly connected to the portion 54 and overlies a small section of the hole 38. When a media plate is moved upwardly through the hole 38 it will contact the opposed portions 56, deflecting them upwardly until the media plate has passed them by. The portions 56 fall back to the positions shown in FIG. 3 and the media plate (or stack thereof) is lowered so that the media plate (or the lowermost one of a stack) can rest on the upper surface of the portions 56 to prevent the media plate (or stack thereof) from falling back through the hole 38. The portion 56 can be hinged to the portion 54 with, or without, the benefit of spring means, such as a torsion spring, which urges the portion 56 towards the supporting position shown in FIG. 3.

Figure 4:
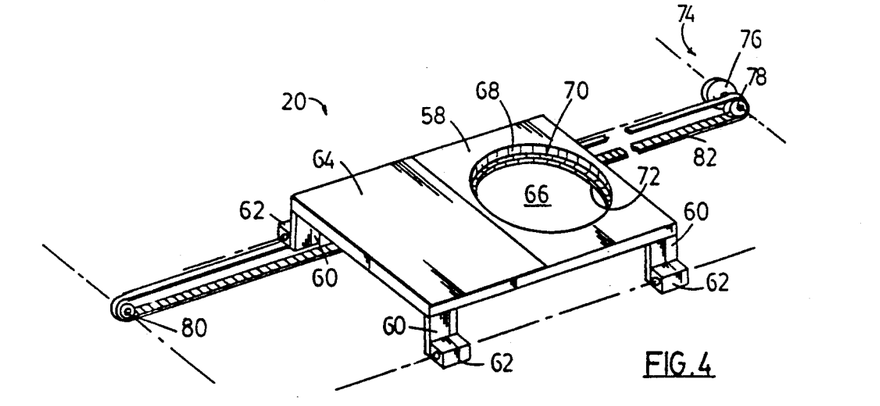
FIG. 4 is a perspective view of the first carriage means of the apparatus.

FIG. 4 illustrates the first carriage means 20 referred to above. The carriage means 20 includes a top plate 58, a plurality of strut members 60, each depending from a corner of the plate 58, and a plurality of linear bearings 62, each being secured in a conventional manner to a respective strut member 60. The linear bearings on one side of the plate 58 will slide on one of the rods 31 of the first bearing way 16 and the linear bearings on the other side of the plate 58 will slide on the other rod 31 of the first bearing way 16. The linear bearings 62 are commercially available and need not be described more fully herein.

One portion of the plate 58 is covered by a smooth sheet 64 which, when the carriage means 20 is mounted on the first bearing ways 16, will be spaced just slightly below the undersurface of the table means upper plate 32. The vertical spacing of the carriage top plate 58 below the table plate 32 is fixed by the height of the strut members 60.

The other portion of the plate 58 is provided with a stepped throughhole 66. The large diameter portion 68 of the hole 66 terminates at an annular step 70 which in turn defines the smaller diameter portion 72 of the hole. The smaller diameter portion 72 is sized so as to easily pass the body or plate portion of a media plate therethrough while the diameter of the portion 68 is such as to accept the cover portion of a media plate, the cover resting on the step 70 as the plate portion passes downwardly through the hole 66.

Movement of the first carriage means 20 is achieved by first drive means 74 which includes a reversible stepper motor 76 secured in a conventional manner to a frame end plate 30, a drive pulley or sprocket 78 driven by the motor 76, an idler pulley or sprocket 80 secured to the other frame end plate 30, and a chain or toothed timing belt 82 attached at its ends to the carriage means 20 and entrained about the sprockets 78,80. The provision of a suitable commercially available motor controlled by appropriate electronic means is well within the purview of a competent engineer.

Figure 5:
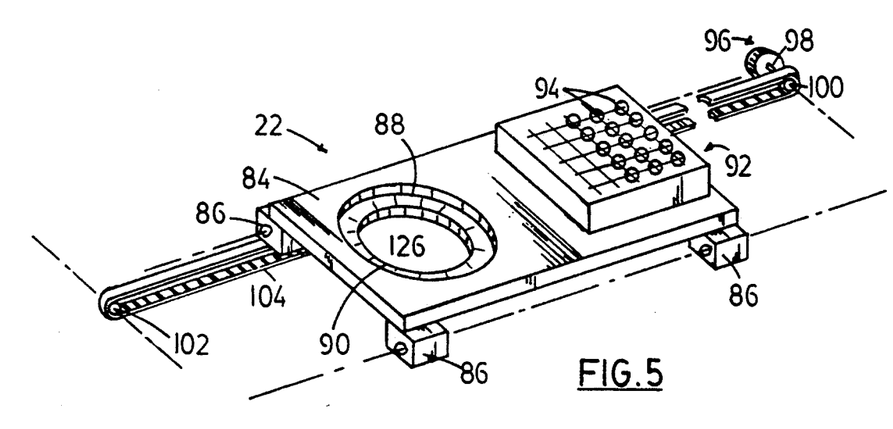
FIG. 5 is a perspective view of the second carriage means of the apparatus.

FIG. 5 illustrates the second carriage means 22 of the present invention. The second carriage means includes a top plate 84 and a plurality of linear bearings 86, each secured to the plate 84 at a respective corner thereof. The linear bearings on one side of the plate 84 will slide on one of the rods 31 of the second bearing ways 18 while the linear bearings on the other side of the plate 84 slide on the other rod 31 of the second bearing ways 18. Since the plate 84 is intended to slide below the first carriage means 20 and since the rods 31 are preferably in the same plane the second carriage means need not having supporting struts as are shown with the first carriage means, although such could be utilized if necessary.

The top plate 84 is provided with a circular recess 88 therein, the diameter being essentially the same as smaller diameter portion 72 of hole 66 in the first carriage means 20. The recess 88 has an annular bottom shoulder 90 on which a plate portion of a media plate can rest. Also provided is a commercially available inoculant block 92 having a plurality of recesses 94 therein containing the inoculant to be transferred to the media plates. The plate 84 can be provided with appropriate means for positively locating the block 90 thereon, the locating means used depending on the particular block to be carried by the plate 84.

As with the first carriage means a drive means 96 is provided for moving the second carriage means along the bearing ways 18. A reversible stepper motor 98 drives a pulley or sprocket 100, the motor 98 being secured to one frame end wall 30. An idler pulley or sprocket 102 is secured to the other frame end wall 30 and a toothed timing belt or chain 104 is entrained about the pulleys or sprockets 100,102 with the ends thereof attached to the second carriage means 22. The motor 98 can be the same as the motor 76, controlled in an analogous manner.

Figure 6:
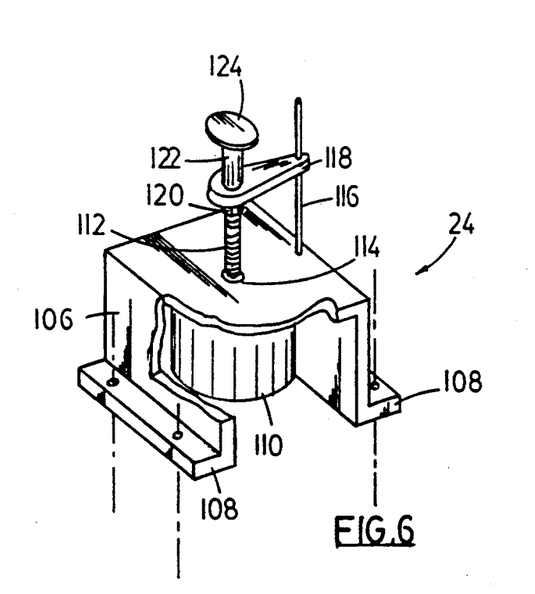
FIG. 6 is a partial perspective view of the transfer means of the apparatus.

FIG. 6 illustrates the transfer means 24. It includes a mounting bracket 106 which is shown as an inverted U-shape with outwardly extending flanges 108 through which bolts or screws can pass for securing the bracket to the work surface below the hole 38 in the table means 14. The bracket 106 mounts a stepper motor 110 therebelow, the motor driving a threaded rod 112 that extends vertically through a hole 114 in the bracket. Parallel to the threaded rod 112 is a vertically extending guide rod 116. A guide member 118 spans the distance between the threaded and guide rods 112,116 and is adapted to slide vertically on the guide rod 116. Affixed to the underside of the guide member 118 is a nut 120 threadedly engaged with the threaded rod 112 so that, as the rod 112 rotates, the nut and the guide member affixed thereto will move vertically along the rod 112. The guide rod 116 keeps the guide member 118 from rotating as the rod 112 rotates.

An annular or cylindrical tube 122 is affixed to the upper surface of the guide member 118 and fits over the portion of the threaded rod 112 that is above the guide member 118. At the upper end thereof the tube 122 mounts a relatively small circular disk 124 which has a diameter less than the opening 126 in the second carriage means 22 as defined by the annular shoulder 90. The diameter of the disc 124 must also be less than the smaller diameter 72 in the first carriage means 20.

Figure 7:
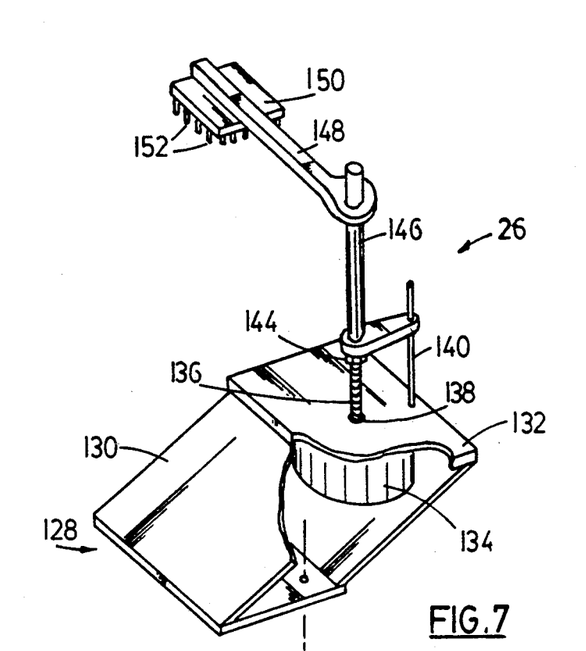
FIG. 7 is a partial perspective view of the action means of the apparatus.

FIG. 7 illustrates the action means 26, used in this case to inoculate media plates with inoculant contained in the block 92. The means 26 includes a stand 128 which can be bolted or screwed to the work surface. As shown, the sides 130 of the stand slope upwardly and outwardly so that the top wall 132 thereof can be located adjacent the first bearing ways 16.

A reversible commercially available stepper motor 134 is mounted to the top wall 132 therebelow, and drives a threaded rod 136 that extends vertically through hole 138 in the top wall 132.

A guide rod 140 extends vertically from top wall 132 and a guide member 142 bridges the gap between the guide and threaded rods, member 142 sliding smoothly on guide rod 140 at one end and passing the threaded rod 136 therethrough at the other end. A nut 144 is affixed to the underside of member 142 and threadedly engages the rod 136 so that rotation of the rod will move the guide member vertically relative to the top wall 132.

A cylindrical tube 146 is affixed to the guide member's upper surface and receives the upper portion of the threaded rod 136 therein. A radially extending arm 148 is secured to the upper end of tube 146 and projects over the bearing ways 16,18. At its distal end the arm carries a removable inoculant head 150 which is provided with a plurality of depending rods 152, there being one rod for each recess 94 of the inoculant block 92. Typically the inoculant head 150 will be provided with the block 92 and will replace a previous head 150 whenever a new inoculant block 92 is to be used.

The operation of the described apparatus will now be described with particular reference to FIGS. 8A to 8G which represent partial longitudinal sections of the table 14, the first carriage means 20 and the second carriage means 22. Certain portions of the apparatus, such as the bearing ways, are omitted and other portions of the apparatus, such as the transfer means, are shown only when they are performing a function, all for the sake of clarity and ease of understanding.

Figure 8A:
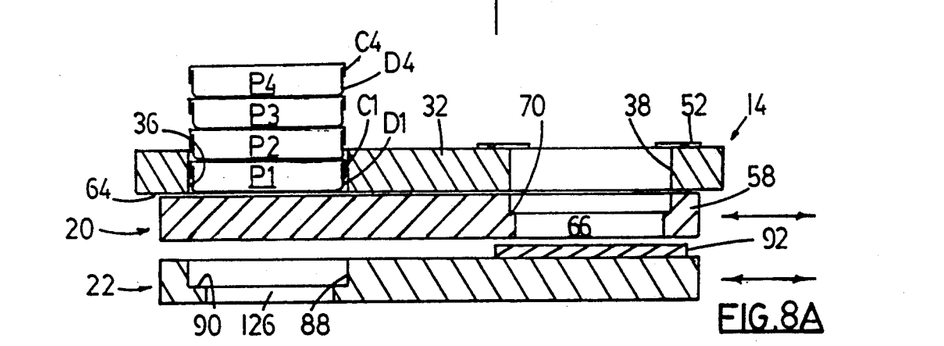
FIGS. 8A-8G illustrate in longitudinal partial cross-section the operation of the apparatus of this invention.

FIG. 8A shows the apparatus as it would appear prior to actuation in its inoculating guise. A plurality (four are shown) of media plates P1-P4 are illustrated as being stacked, with the lowermost plate P1 being received in the table means hole 36 and resting on the plate 64 of the first carriage means 20. The second carriage means 22 is at rest below the first carriage means. Each media plate P1-P4 is sterilized, contains an appropriate culture medium within the dish-like plate portion D1-D4, and is covered by a loose-fitting cover portion C1-C4. A typical media plate would be a standard petri dish.

Figure 8B:
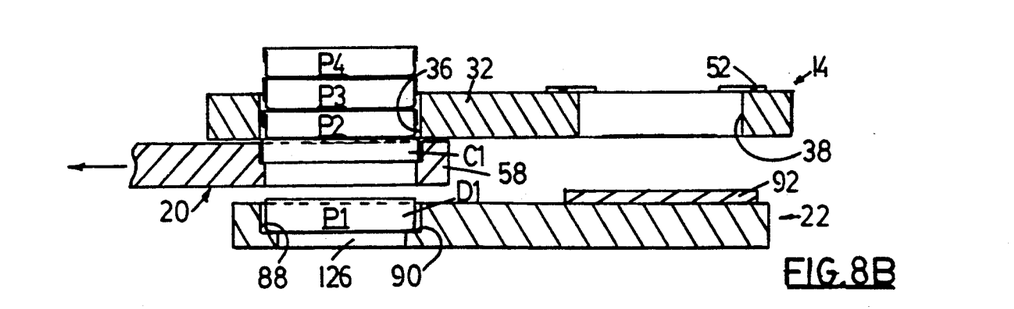

FIG. 8B shows the apparatus after the first carriage means 20 has moved to the left, the motor 76 having effected such movement through the belt 82 after receiving appropriate electronic signals from a controller (not shown). The first carriage means stops below the stack of plates and the lowermost plate P1 falls into the hole 66 in the plate 58, the rest of the stack descending along with the lowermost plate P1. Because of the relative diameters 68,72, the plate position D1 of the media plate P1 will fall through the plate 58 of the first carriage means to come to rest on the annular shoulder 90 of the second carriage means 22. The cover portion C1 of the media plate is of a larger diameter than the plate portion D1 and will be restrained from falling through the first carriage means by the shoulder 70, coming to rest thereon. In this manner the cover portion C1 has been removed from the plate portion D1 so that further processing thereof can take place.

Figure 8C:
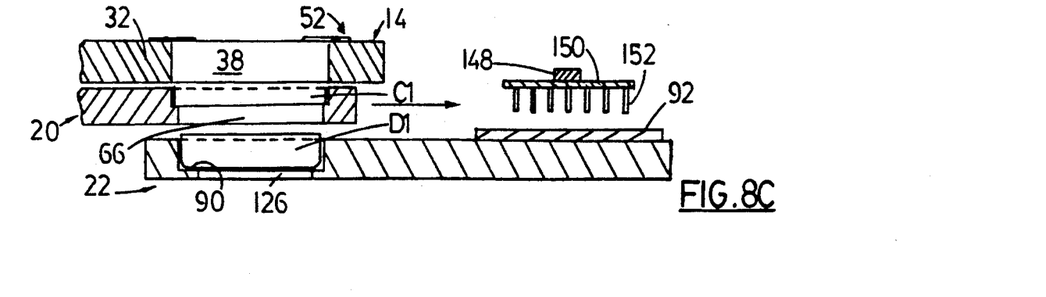

FIG. 8C shows that the first and second carriage means 20,22 have both moved to the right so that the first carriage means is again in the position of FIG. 8A and so that the inoculant block 92 is away from the table means 14, below the arm 148 and its head 150. Movement of the carriage means 20,22 is effected by the stepper motors 76,98 respectively under instruction from the controller. As the first carriage means 20 moves to the right the plate 64 will slide under the next lowermost media plate P2 so as to support the stack of remaining media plates P2-P4 thereon.

Figure 8D:
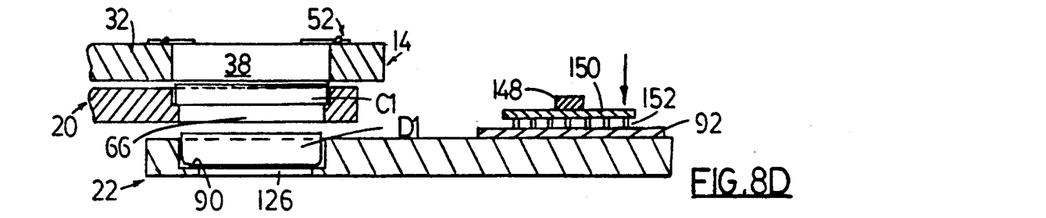

FIG. 8D shows that the arm 148 has descended due to operation of the motor 134 so that each of the depending inoculant rods 152 is inserted into a respective recess 94 of the block 92, a small amount of inoculant within each recess adhering to the end of the inserted rod 152.

Figure 8E:
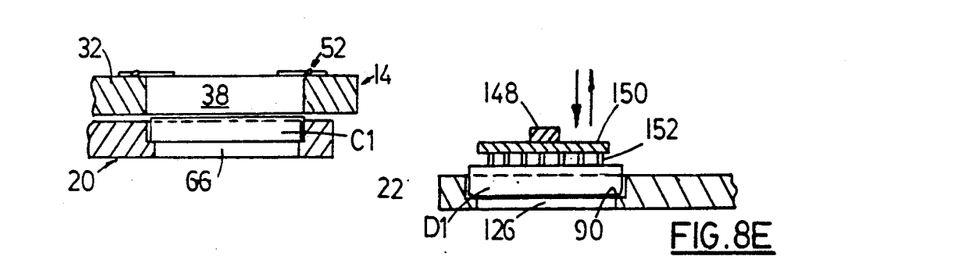

FIG. 8E shows that the arm 148 has been raised; that the second carriage means 22 has been moved further to the right by motor 98 so that the open plate portion D1 is below the head 150 and depending rods 152; and that the arm 148 has been lowered so that the rods 152 have entered the plate portion D1 so as to inoculate the culture medium therein.

Figure 8F:
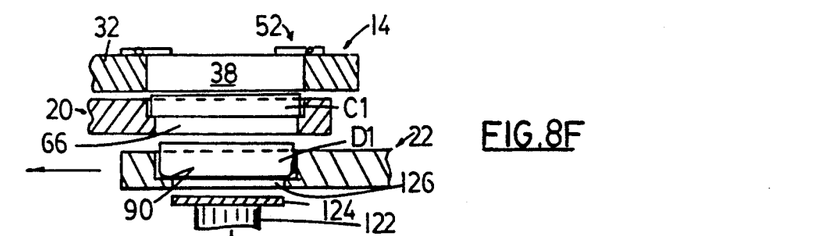

In FIG. 8F it is seen that the second carriage means has been moved to the left so that the plate portion D1 underlies the cover portion C1 still held by the first carriage means 2D below the hole 38 of the table means 14. The transfer means 24 has been actuated and the disc 124 is rising towards the inoculated plate portion D1.

Figure 8G:
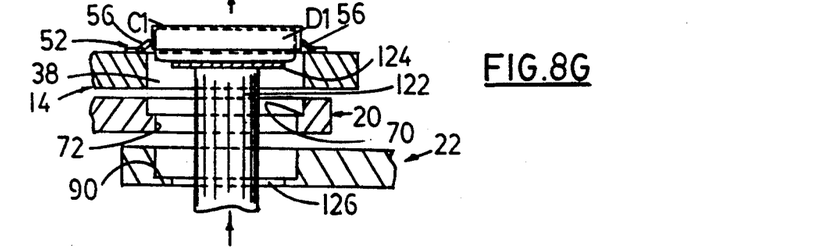

FIG. 8G shows that the disc 124 has risen sufficiently, moved by the stepper motor 110, to pass through the second carriage means to contact the bottom of the inoculated plate portion D1 resting on the shoulder 90, to thereafter elevate the plate portion D1 through the opening 72 in the first carriage means into contact with the cover portion C1 resting on the shoulder 70, and to elevate the now-covered inoculated media plate P1 through the hole 38 in the table means. As the plate P1 passes the hinged supports 52 the moveable portion 56 thereof is deflected upwardly by the passing plate until the plate P1 has passed completely by, following which the portions 56 fall back to their rest positions on the upper plate 32. Then the disk 124 is lowered so that the inoculated plate P1 descends to rest on the supports 52, the disc 124 then descending completely past the first and second carriage means whereby the apparatus can repeat the foregoing steps with the next media plate P2.

Figure 9:
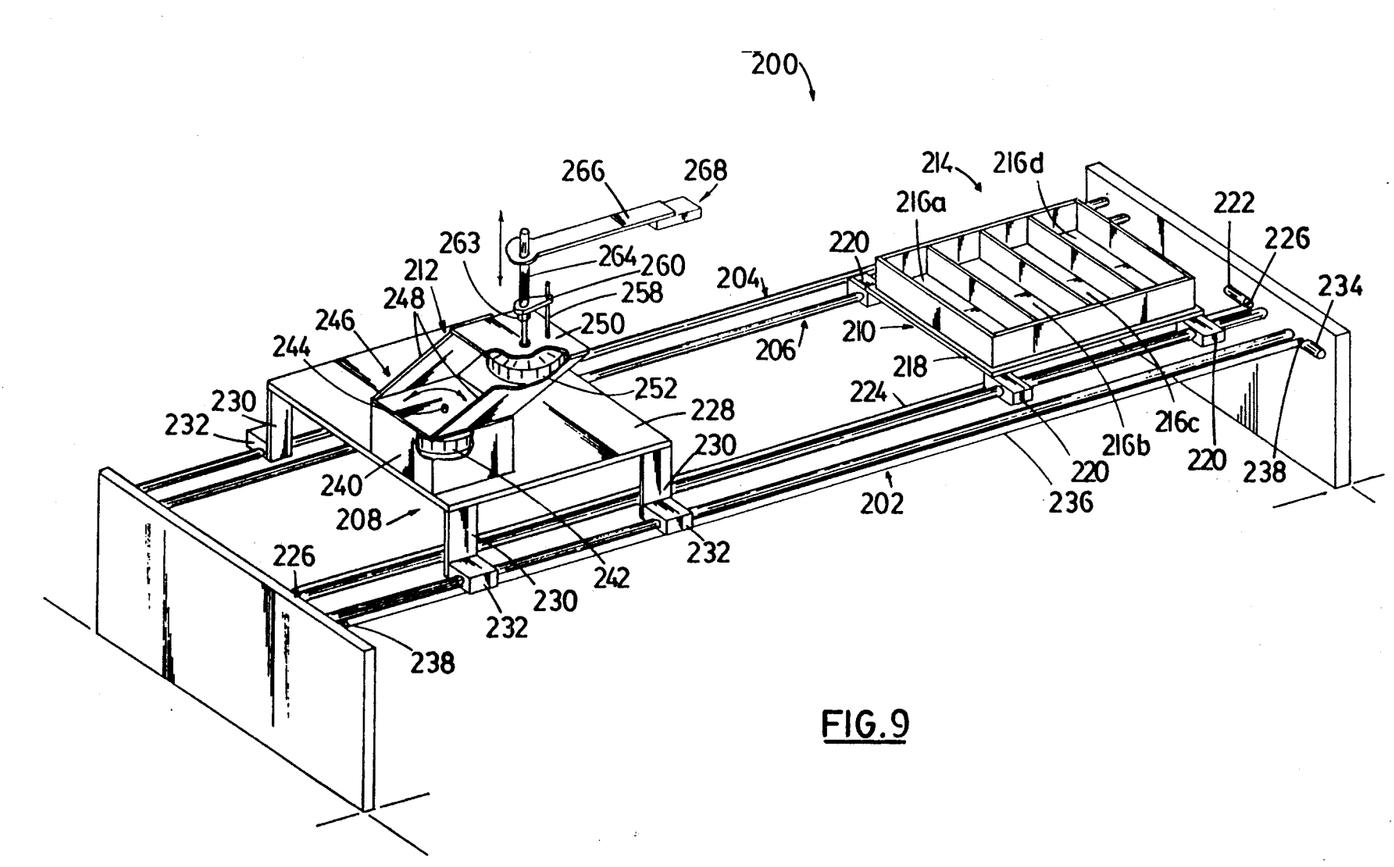
FIG. 9 is a perspective view, similar to FIG. 1, of an alternative embodiment of the invention.

FIG. 9 illustrates another embodiment of the present invention which utilizes many of the previously described components but in a different configuration, thereby demonstrating the versatility of the invention.

The apparatus 200 of FIG. 9 utilizes a frame means 202 including parallel bearing ways 204,206, a first carriage means 208 supported by the bearing ways 204 for independent movement therealong, and a second carriage means 210 supported by the bearing ways 206 for independent movement therealong. Action means 212 are supported by one of the carriage means for performing certain desired functions, particularly with reference to the other carriage means. As with the first embodiment control of the movements of the carriage means and the action means is under the control of a suitably programmed microcomputer, not shown.

One function that might be performed by the apparatus 200 could be the sequential immersion of objects, such as mounted test samples, in a number of different solutions. One configuration to perform that function is shown in FIG. 9 wherein the second carriage means 210 is provided with a replaceable container 214 separated into a plurality of individual compartments 216a, b, c, d each of which can receive a particular solution as desired. The second carriage means includes a top plate 218 supported by linear bearings 220 which in turn slide on the bearing ways 206, as before. A stepper motor 222 drives a chain or belt 224 connected at each end to the second carriage means 210 and entrained about suitable sprockets or pulleys 226 at each end so as to provide desired movement of the carriage means 210 along the bearing ways 206.

The first carriage means 208 has a top plate 228 supported by struts 230 and linear bearings 232 which slide on the bearing ways 204. Stepper motor 234, chain or belt 236 and sprockets or pulleys 238 are provided as before for independent controlled movement of the first carriage means 208 along the bearing ways 204 as desired or required.

It should be mentioned here that the frame means 202, bearing ways 204,206, first carriage means 208, and second carriage means 210 can be exactly the same components 12, 16, 18, 20, and 22 as described for the first embodiment. The container 214 can merely sit on the second carriage means without requiring any modifications thereto.

As indicated previously, the action means 26 of the first embodiment can be moved from its work station. In the embodiment of FIG. 9 the action means 212 can be the same action means 26 or it can be a separate action means, particularly if more functions are to be performed thereby.

In FIG. 9 a hollow mounting block 240 is secured to the top plate 228 of the first carriage means 208 so as to elevate the action means 212. The block 240 contains a stepper motor 242 for imparting reversible rotary motion to its shaft 244. A stand 246 is attached to the shaft 244, the sides 248 of the stand sloping upwardly and outwardly as before. Below the top wall 250 of the stand is mounted a reversible stepper motor 252 which drives a threaded rod 254 that extends vertically through the hole 256 in the top wall 250.

A guide rod 258 extends vertically from top wall 250 and a guide member 260 bridges the gap between the guide and threaded rods; member 260 sliding smoothly on guide rod 258 at one end and passing the threaded rod 254 therethrough at the other end. A nut 262 is affixed to the underside of member 260 and threadedly engages the rod 254 so that rotation of the rod will move the guide member 260 vertically relative to the top wall 250.

A cylindrical tube 264 is provided above the guide member 260 and receives the upper portion of the threaded rod 254 therein. A radially extending arm 266 is secured to the upper end of the tube 264 and projects away therefrom a distance sufficient to clear the edges of the first carriage means. At its distal end the arm 266 carries a removable gripper means, symbolically shown by block 268, which is used to grip whatever object is to be handled by the arm 266. The shape of the gripper means will, of course, depend on the shape of the object to be handled.

In operation of this embodiment, and with the compartments 216a, b, c, d containing suitable solutions, the first carriage means 208 can be moved suitably so that the stand 246 can be rotated to position the gripper means above an object to be treated. The arm 266 is lowered to bring the gripper means 268 into proximity with the object to be treated. Such objects might be provided, for example, in a tray or rack positioned adjacent the bearing ways 204. The gripper means 268 may automatically pick up the object to be treated or the object may be connected to the gripper means by an operator or attendant.

Once the object has been gripped the arm 266 is raised, the stand 246 is rotated and the first carriage means 208 is moved along the bearing ways 204 so that it approaches the second carriage means 210. At an appropriate position it is stopped and the arm 266 is lowered to immerse the object in the contents of first compartment 216a. Thereafter, the arm 266 is raised and the carriage means is advanced so that the object can be immersed in the contents of the second compartment 216b. Once all treatments have been completed the stand 246 is rotated and the arm 266 is lowered to bring the treated object to a suitable rest area for drying or further processing. The treatment process can then begin again with a new object.

It is evident that the components of this invention can be assembled into various configurations so as to perform a multitude of diverse repetitive tasks. As is apparent from the second disclosed embodiment it is not always necessary to utilize all of the components of the invention to achieve an operable and effective apparatus. Furthermore, several functions could be performed by any one configuration merely by changing the sequence of operations via modifications to the operating computer programme. It is clear, therefore, that the number of modifications possible with the present invention will depend largely on the imagination of the operator and that the embodiments disclosed herein are intended to be illustrative rather than restrictive. Accordingly, the protection to be afforded the present invention is to be determined from the claims appended hereto.

The embodiments of the invention in which an exclusive property or privilege is claimed are defined as follows:

1. Laboratory apparatus for performing repetitive tasks comprising: a frame; a table removably located in said frame; first parallel bearing ways in said frame below and parallel to said table; second parallel bearing ways in said frame below and parallel to said table; first carriage means supported by said first bearing ways for independent movement therealong; second carriage means supported by second bearing ways for independent movement therealong in a plane below and parallel to said first carriage means; independently operable transfer means for transferring objects as desired between said table and a selected one of said carriage means or between said first and second carriage means; action means at a work station adjacent to or spaced from said table for performing an operation on an object positioned on said table or on said carriage means; and means for coordinating the movement of said first and second carriage means, said transfer means and said action means in accordance with repetitive tasks to be performed.

2. Apparatus according to claim 1, in which said table can support a source supply of said objects and can also support objects on which an operation has been performed by said action means.

3. Apparatus according to claim 2, in which said action means is vertically reciprocable and can carry selected interchangeable means for performing different operations on the objects at said work station.

4. Apparatus according to claim 2, in which said action means is vertically reciprocable, is rotatable on a generally vertical axis, and can carry selected interchangeable means for performing different operations on the objects at said work station.

5. Apparatus according to claim 4, wherein said action means comprises a vertically oriented shaft, an arm carried on said shaft for vertical reciprocal movement thereon, said arm being adapted to mount said interchangeable means thereon, and an independently controllable reversible stepper motor for moving said arm vertically on said shaft.

6. Apparatus according to claim 2, wherein said transfer means is vertically reciprocable for moving objects carried thereby between said first carriage means and said table, and between said first carriage means and said second carriage means.

7. Apparatus according to claim 6, in which said transfer means comprises a vertically oriented threaded rod member carrying a guide member with a threaded nut thereon, an object transfer member carried by said guide member; and a reversible independently controllable stepper motor connected to said rod member to effect rotation thereof for consequent raising or lowering of said guide member and said transfer member.

8. Apparatus according to claim 1, in which a separate, individually controllable, drive means is provided for each of said first carriage means, said second carriage means, said transfer means and said action means.

9. Apparatus according to claim 1, in which a separate, individually controllable stepper motor is provided to drive each of said first carriage means, said second carriage means, said transfer means and said action means, and in which said coordinating means includes a microcomputer programmed to operate said stepper motors in a predetermined sequence to achieve performance of said repetitive tasks.

10. Apparatus according to claim 1 in which each of said parallel bearing ways comprises a pair of parallel rod members mounted in said frame, each of said carriage means includes a generally rectangular plate mounting fore and aft linear bearings adapted to slide on the rod members, and in which movement of a carriage means on the rod members is effected by an independently controllable reversible stepper motor mounted at one end of the frame, the motor carrying a rotatable sprocket or pulley member for driving a flexible chain or timing belt the ends of which are connected to the carriage means, said chain or belt being entrained about an idler sprocket or pulley member mounted at the other end of the frame.

11. Apparatus according to claim 1, wherein said table can support a plurality of sterilized media plates and can receive inoculated media plates; said first carriage means can receive and retain a cover portion of a media plate transferred from said table; said second carriage means can receive and support a plate portion of a media plate transferred thereto from said table via said first carriage means; and wherein said independently operable transfer means can transfer plate portions between said second carriage means and said table; said action means comprising inoculator means at a work station spaced laterally from said table for inoculating a plate portion supported by said second carriage means; and said coordinating means operating to coordinate the movement of said first and second carriage means, said transfer means and said inoculator means to effect inoculation of said sterilized media plates and to return the inoculated media plates to said table.

12. Laboratory apparatus for use in inoculating a plurality of media plates comprising: a frame; a table mounted in said frame at a fixed location for supporting a plurality of sterilized media plates and for receiving inoculated media plates; first parallel bearing ways in said frame below and parallel to said table; second parallel bearing ways in said frame below and parallel to said table; first carriage means supported by said first bearing ways for independent movement therealong and for receiving and retaining a cover portion of a media plate transferred thereto from said table; second carriage means supported by said second bearing ways for independent movement therealong in a plane below and parallel to said first carriage means and for receiving and supporting a plate portion of a media plate transferred thereto from said table via said first carriage means; independently operable transfer means for transferring plate portions between said second carriage means and said table; inoculator means at a work station spaced laterally from said table for inoculating a plate portion supported by said second carriage means; and means for coordinating the movement of said first and second carriage means, said transfer means and said inoculator means to effect inoculation of said sterilized media plates and to return the inoculated media plates to said table.

13. Apparatus according to claim 12, in which said transfer means is vertically reciprocal for moving plate portions between said second and first carriage means and for moving inoculated media plates between said first carriage means and said table.

14. Apparatus according to claim 13, in which said first carriage means has an opening therethrough, said opening being sized to pass a descending plate portion therethrough and to prevent a cover portion from passing therethrough so as to effect automatic retention of a cover portion thereon, said second carriage means carrying the plate portion thereon to and from said work station.

15. Apparatus according to claim 14, in which said transfer means comprises a vertically oriented threaded rod member carrying a guide member with a threaded nut thereon, a media plate transfer member carried by said guide member, and a reversible independently controllable stepper motor connected to said rod member to effect rotation thereof for consequent raising or lowering of said guide member and said transfer member.

16. Apparatus according to claim 15, in which said inoculator means comprises a vertically oriented threaded shaft, an arm carried by said shaft for vertical reciprocal movement thereon, said arm removably mounting a commercially available inoculator head thereon, and an independently controllable reversible stepper motor for moving said arm vertically on said shaft.

17. Apparatus according to claim 12, in which a separate, individually controllable, reversible stepper motor is provided to drive each of said first carriage means, said second carriage means, said transfer means and said inoculator means, and in which said coordinating means includes a microcomputer programmed to operate said stepper motors in a predetermined sequence to effect inoculation of said media plates and to return inoculated media plates to said table.

18. Apparatus according to claim 12, in which each of said parallel bearing ways comprises a pair of parallel rod members mounted in said frame, each of said carriage means includes a generally rectangular plate mounting fore and aft linear bearings adapted to slide on the rod members, and in which movement of a carriage means on the rod members is effected by an independently controllable reversible stepper motor mounted at one end of the frame, the motor carrying a rotatable sprocket or pulley member for driving a flexible chain or timing belt the ends of which are connected to the carriage means, said chain or belt being entrained about an idler sprocket or pulley member mounted at the other end of the frame.

* * * * *